US00PP32269P3

(12) United States Plant Patent
Adams

(10) Patent No.: US PP32,269 P3
(45) Date of Patent: Oct. 6, 2020

(54) RASPBERRY PLANT NAMED 'NOBILITY'

(50) Latin Name: *Rubus idaeus*
Varietal Denomination: NOBILITY

(71) Applicant: PLANT SCIENCES, INC., Watsonville, CA (US)

(72) Inventor: Scott W. Adams, Watsonville, CA (US)

(73) Assignee: PLANT SCIENCES, INC., Watsonville, CA (US)

( * ) Notice: Subject to any disclaimer, the term of this patent is extended or adjusted under 35 U.S.C. 154(b) by 0 days.

(21) Appl. No.: 16/602,483

(22) Filed: Oct. 18, 2019

(65) Prior Publication Data

US 2020/0137938 P1 Apr. 30, 2020

Related U.S. Application Data

(60) Provisional application No. 62/750,904, filed on Oct. 26, 2018.

(51) Int. Cl.
*A01H 5/08* (2018.01)
*A01H 6/74* (2018.01)

(52) U.S. Cl.
USPC ..... Plt./203
CPC ..... *A01H 6/7499* (2018.05)

(58) Field of Classification Search
USPC ..... Plt./203, 204
See application file for complete search history.

*Primary Examiner* — Susan McCormick Ewoldt
(74) *Attorney, Agent, or Firm* — Foley & Lardner LLP

(57) ABSTRACT

This invention relates to a new and distinct fall bearing variety of raspberry plant named 'NOBILITY'. The new variety is primarily adapted to the growing conditions of the central coast of California and is characterized by the following: early-season primocane production with medium sized fruit of medium-red coloration. Fruit is of consistent conic shape, releases easily from receptacle, is glossy and possesses very good flavor. Foliage is flat to slightly convex, medium green; possessing medium rugosity, weak gloss and mostly 3-foliates. Primocanes have a weak waxy coat, medium thorn density of long spine length and have weak anthocyanin coloration.

4 Drawing Sheets

Latin name of the genus and species of the plant clamed: *Rubus idaeus*.

Variety denomination: 'NOBILITY'.

BACKGROUND OF THE INVENTION

The present invention relates to a new and distinct fall bearing raspberry variety designated as 'NOBILITY'. This new variety is a result of a controlled cross made in Watsonville, Calif. by the inventor, Scott W. Adams, in 2009 between raspberry variety designated '04.3721' (unpatented) as the female parent and raspberry variety 'RADIANCE' (patented, U.S. Plant Pat. No. 20,342) as the male parent in an ongoing breeding program. The variety is botanically known as *Rubus idaeus* and was tested as 'PS-09.082-06' and 'PS-8206'.

The seedling resulting from the aforementioned cross was asexually propagated by dormant canes in Santa Cruz County, Calif. and was subsequently selected by the inventor from a controlled breeding plot in Watsonville, Calif. in 2011. After its selection, the new variety was further asexually propagated by dormant canes, roots and non-dormant root shoot cuttings in Santa Cruz County, Calif., San Joaquin County, Calif. and Siskiyou County, Calif. The new variety was then extensively tested over the next several years in fruiting fields in Santa Cruz County, Calif. and Ventura County, Calif. This propagation has demonstrated that the combination of traits disclosed herein as characterizing the new variety are fixed and remain true to type through successive generations of asexual reproduction.

BRIEF SUMMARY OF THE INVENTION

'NOBILITY' is primarily adapted to the climate and growing conditions of the central coast of California. This region provides the necessary year-round temperatures required for it to produce and maintain a strong vigorous plant and to remain in fruit production from July through December on primocanes and in the ensuing year from May through July on floricanes. The following traits have been repeatedly observed and are determined to be unique characteristics of 'NOBILITY', which in combination distinguish this raspberry plant as a new and distinct variety:

1. Long spine length
2. Short internode length
3. Early primocane time of fruiting
4. Medium red fruit color
5. Weak primocane glaucosity
6. Very good flavor The raspberry variety that is believed to be most closely related to the new raspberry variety 'NOBILITY' is the raspberry variety 'GRANDEUR' (patented, U.S. Plant Pat. No. 20,459). In comparison to the similar raspberry variety 'GRANDEUR', 'NOBILITY' differs by the following combination of characteristics described in Table 1:

COMPARISON BETWEEN NOBILITY AND GRANDEUR

TABLE 1

| Characteristic | 'NOBILITY' | 'GRANDEUR' (US PP20,459) |
|---|---|---|
| Primocane waxy coat (glaucosity) | Weak | Absent to very weak |

TABLE 1-continued

| Characteristic | 'NOBILITY' | 'GRANDEUR' (US PP20,459) |
|---|---|---|
| Predominate number of leaflets | Mostly 3 | Always 3 |
| Primocane time of fruiting | Early | Medium |
| Rugosity | Medium | Strong |
| Color mature fruit | RHS 45A Medium red | RHS 42A Medium red |
| Thorn length at central 1/3 (mm) | 3.04 | 0.76 |
| Floricane coloration (true) | RHS 165B Greyed-orange group | RHS 164A Greyed-orange group |

'NOBILITY' differs from its parents, '04.3721' and 'RADIANCE' by the following combination of characteristics described in Table 2:

COMPARISON BETWEEN NOBILITY, 04.3721 AND RADIANCE

TABLE 2

| Characteristic | 'NOBILITY' | '04.3721' | 'RADIANCE' (US PP20,342) |
|---|---|---|---|
| Productivity | Medium | Medium | Medium |
| Glossiness (fruit) | High | Medium | Medium |
| Firmness (fruit) | High | Medium to low | High |
| Adherence of receptacle | Very weak | Strong | Weak |
| Primocane time of fruiting | Early | Medium | Early |
| Fruit size | Medium | Large | Small |
| Flavor | Very good | Poor | Excellent |

For identification, a series of molecular markers have been determined for this new variety.

BRIEF DESCRIPTIONS OF THE DRAWINGS

The accompanying color photographs illustrate the overall appearance of typical specimens of the new raspberry variety 'NOBILITY' at various stages of development as true as reasonably possible with color reproductions of this type. Color in the photographs may differ slightly from the color value cited in the detailed botanical description which accurately describes the color of 'NOBILITY'. The depicted plant and plant parts of the new raspberry variety 'NOBILITY' were taken in Watsonville, Calif. and are approximately two to sixteen months old:

DETAILED BOTANICAL DESCRIPTION

Figure 1:
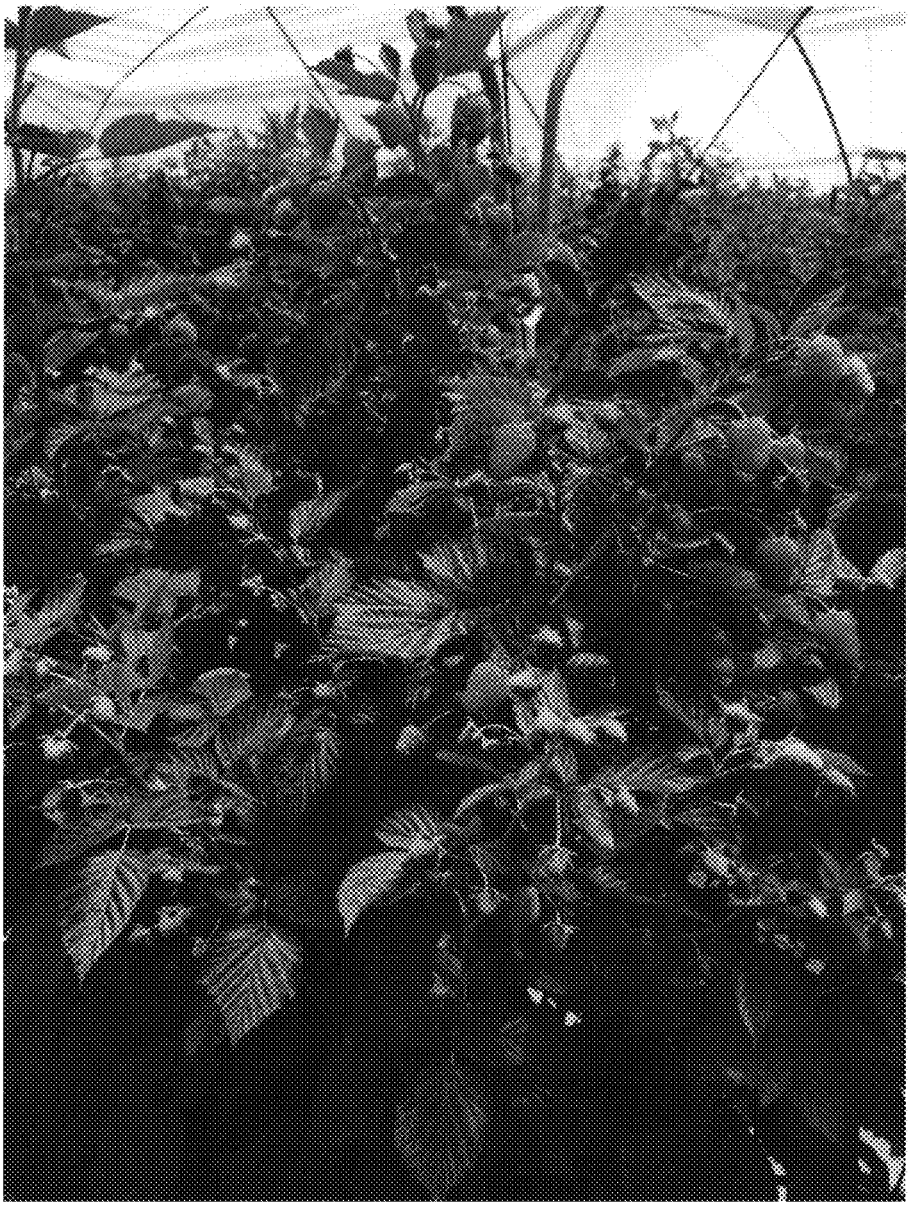
FIG. 1 shows typical primocane foliage and fruit color, foliate and rugosity characteristics of 'NOBILITY' taken in the month of July 2018.
Figure 2:
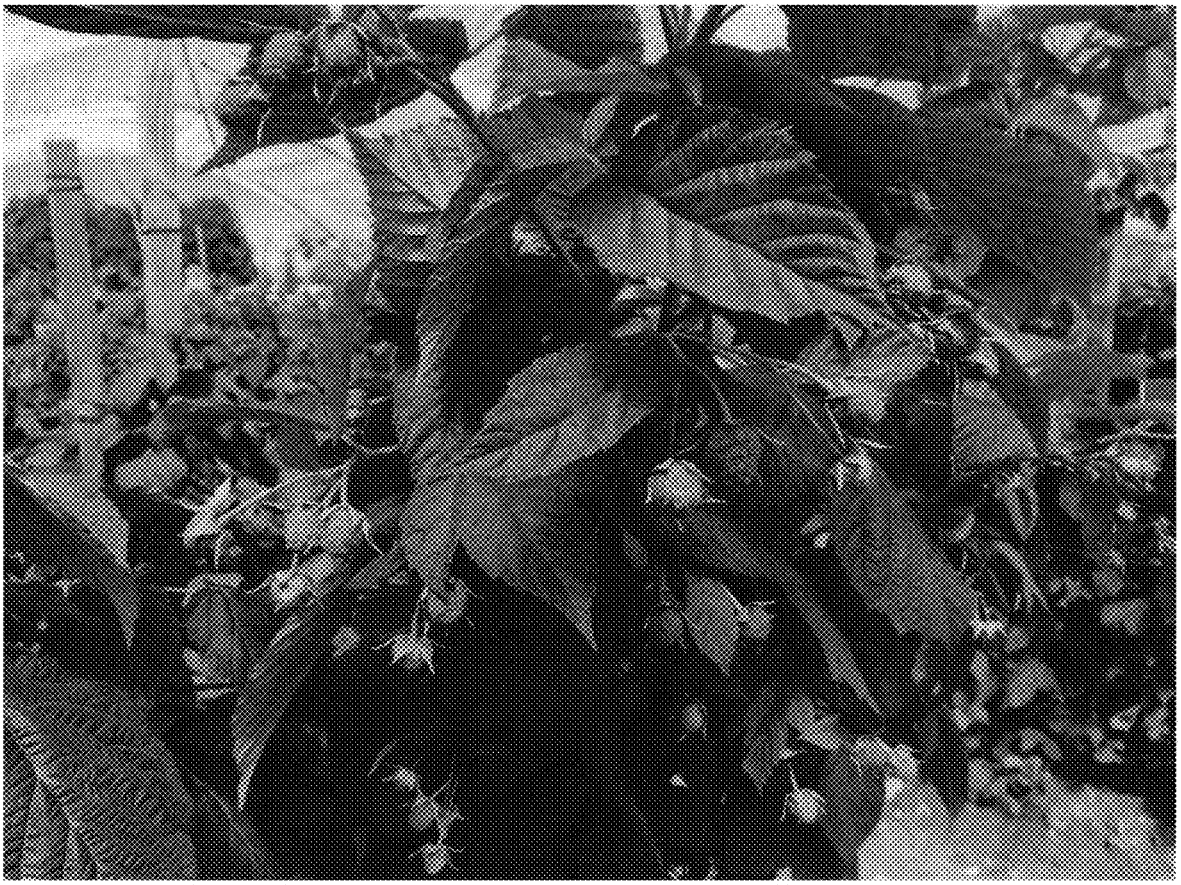
FIG. 2 shows typical green fruit, pedicels and peduncles of 'NOBILITY' taken in the month of September 2019.
Figure 3:
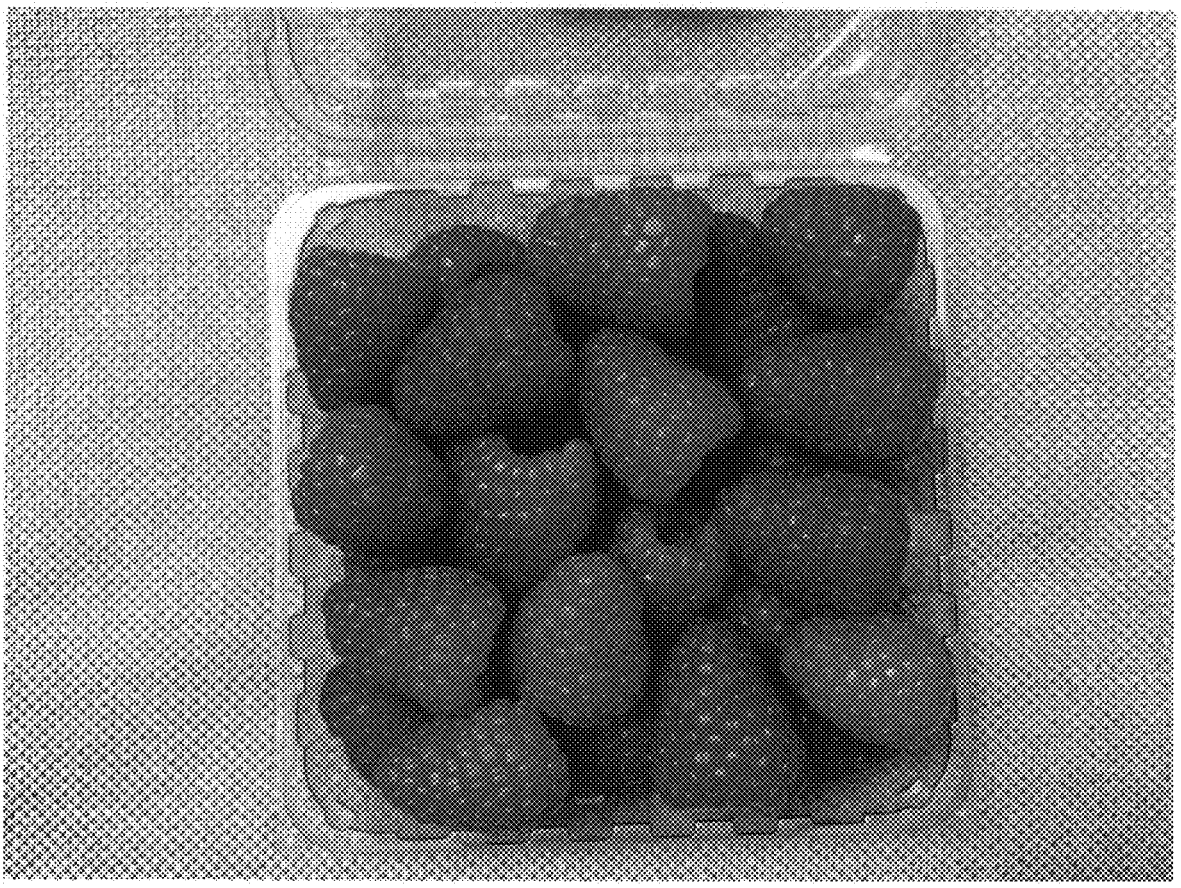
FIG. 3 shows typical harvested fruit of 'NOBILITY' taken in the month of July 2018.
Figure 4:
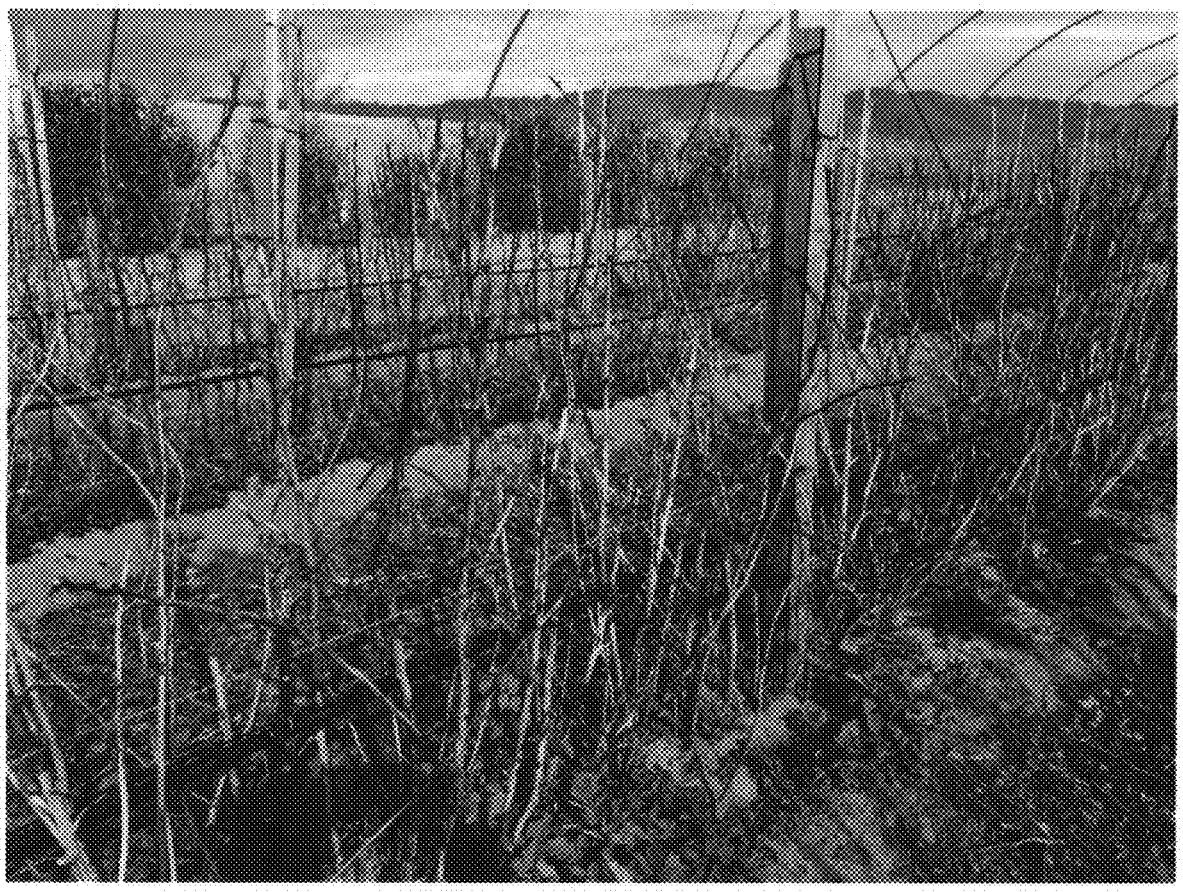
FIG. 4 shows typical dormant cane color characteristics of 'NOBILITY' taken in the month of February 2019.

'NOBILITY' has not been observed under all possible environmental conditions. The characteristics of the new variety may vary in detail, depending upon variations in environmental factors, including weather (temperature, humidity and light intensity), day length, soil type, and location.

The aforementioned photographs, together with the following description of the new raspberry variety 'NOBILITY', unless otherwise noted, are based upon observations taken during the 2018-2019 growing season in Watsonville, Calif. Primocane measurements and ratings were taken from plants of 'NOBILITY' dug from a nursery located in Siskiyou County, Calif. during the middle of October 2017 and planted approximately three to four weeks later in Watsonville, Calif. The approximate age of the observed primocane plants is seven to eight months. Floricane measurements and ratings were taken from the same planting of 'NOBILITY' at an approximate age of sixteen to eighteen months. Yield observations and fruit quality characteristics are averaged from three years of data collected from the 2017 through 2019 production seasons. Flower measurements and characteristics are from secondary flowers unless otherwise noted. Fruit characteristics and measurements are from secondary fruit unless otherwise noted. Foliage characteristics and measurements are from 3-foliate foliage unless otherwise noted.

Color terminology where noted follows The R.H.S. Colour Chart Fifth Edition, Royal Horticultural Society, London, United Kingdom (1966).

The following tables 3-7 describe fruit, plant, foliage, flower and pest/disease characteristics of the new raspberry 'NOBILITY' in comparison to the similar raspberry variety 'GRANDEUR' (patented, U.S. Plant Pat. No. 20,459).

COMPARISON BETWEEN NOBILITY AND GRANDEUR

TABLE 3

FRUIT CHARACTERISTICS

| Characteristic | 'NOBILITY' | 'GRANDUER' (US PP20,459) |
|---|---|---|
| Color mature fruit | RHS 45A Medium red | RHS 42A Medium red |
| Color achenes | RHS 159A Orange-white group | RHS 159A Orange-white group |
| Fruit length (mm) | 23.28 | 22.91 |
| Fruit width (mm) | 20.60 | 20.12 |
| Length/width ratio | 1.13 Longer than broad | 1.14 Longer than broad |
| Seed weight (mg) | 1.79 | 1.75 |
| Drupelets per berry | 79 | 93 |
| Weight of single drupe (g/drupe) | 0.066 | 0.043 |
| Drupe length (mm) | 6.76 | 5.25 |
| Drupe diameter (mm) | 4.96 | 3.86 |
| Relative size of drupes | Large | Medium |
| Fruit size | Medium | Medium |
| Fruit per node | 12 | 15 |
| Predominant shape | Conical | Conical |
| Receptacle length (mm) | 22.66 | 19.15 |
| Receptacle diameter (mm) | 9.09 | 10.32 |
| Receptacle color | RHS 155B White group | RHS 155B White group |
| Evenness of color (fruit) | Even | Even |
| Glossiness | High | Medium |
| Adherence of receptacle | Very weak | Very weak |
| Firmness of flesh | Firm | Very firm |
| Firmness of skin | Firm | Very firm |
| Soluble solids (% brix) | 11.0 | 10.5 |
| Flavor | Very good | Good |

TABLE 4

PLANT CHARACTERISTICS

| Characteristic | 'NOBILITY' | 'GRANDEUR' (US PP20,459) |
|---|---|---|
| General: | | |
| Habit | Upright | Upright |
| Plant height (m) | 1.38 | 1.44 |
| Plant width (cm) | 38 | 45 |
| Time to initiate roots (days) | 12-14 | 12-14 |
| Canes per hill | 10.6 | 6.9 |
| Productivity | Medium | High |
| Self-fruitfulness | Yes | Yes |
| Type of bearing | Fall bearing | Everbearing |
| Primocane: | | |
| Color (true) | RHS 145B Yellow-green group | RHS 145B Yellow-green group |
| Length (cm) | 138.1 | 143.6 |
| Basal diameter (mm) | 19.68 | 21.80 |
| Diameter central 1/3 (mm) | 14.04 | 12.55 |
| Lateral length at central 1/3 (cm) | 35.1 | 43.6 |
| Number of fruiting laterals per cane | 12.1 | 17.4 |
| Total nodes per cane | 34 | 31 |
| Internode length at central 1/3 (mm) | 41.07 | 48.84 |
| Anthocyanin coloration | RHS 59B Red-purple group | RHS 59B Red-purple group |
| Anthocyanin intensity | Weak | Weak |
| Pubescence | Absent | Absent |
| Vegetative bud length (mm) | 7.37 | 11.01 |
| Vegetative bud diameter (mm) | 5.20 | 6.11 |
| Vegetative bud shape | Widely ovate | Widely ovate |
| Vegetative bud color | RHS 187A Greyed-red group | RHS 187A Greyed-red group |
| Strength of waxy coat (glaucosity) | Weak | Absent to very weak |
| Time of flowering | Early | Medium |
| Time of fruiting | Early | Medium |
| Length of fruiting season | Long | Long |
| % of total yield | 49% | 50% |
| Flowering period | Late May to mid-November | Late June to late November |
| Harvest period | Late June to early December | Late July to late December |
| Primocane fruit weight (g) | 4.2 | 3.8 |
| Primocane yield (g/plant) | 2,269 | 2,662 |
| Young Shoots: | | |
| Number (per meter) | 15-20 Medium | 15-20 Medium |
| Anthocyanin presence | Present | Present |
| Anthocyanin coloration | RHS 179B Red-purple group | RHS 179A Greyed-red group |
| Anthocyanin intensity | Weak | Medium |
| Thorns: | | |
| Thorn coloration (tip) | RHS 200A Brown group | RHS 180C Greyed-red group |
| Thorn coloration (base) | RHS 145B Yellow-green group | RHS 145B Yellow-green group |
| Thorn length at central 1/3 (mm) | 3.04 | 0.76 |
| Thorn base at central 1/3 (mm) | 2.02 | 1.53 |
| Thorn presence | Present | Present |
| Thorn density per cm at central 1/3 | 3.70 Medium | 3.38 Medium |
| Thorn texture | Rigid | Rigid |
| Attitude of the tip | Horizontal | Horizontal |

TABLE 4-continued

PLANT CHARACTERISTICS

| Characteristic | 'NOBILITY' | 'GRANDEUR' (US PP20,459) |
|---|---|---|
| Floricane: | | |
| Color (true) | RHS 165B Greyed-orange group | RHS 164A Greyed-orange group |
| Length (cm) | 95.4 | 119.8 |
| Width at central 1/3 (mm) | 13.44 | 12.04 |
| Total nodes per cane | 19 | 18 |
| Internode length at central 1/3 (mm) | 43.00 | 49.13 |
| Fruiting lateral attitude | Erect | Erect |
| Time bud burst | Medium | Medium |
| Time of flowering | Medium | Medium |
| Time of fruiting | Medium | Medium |
| Length of fruiting season | Medium to long | Medium to long |
| % of total yield | 51% | 50% |
| Flowering period | Late April to late June | Late April to late June |
| Harvest period | Late May to late July | Late May to late July |
| Floricane fruit weight (g) | 4.1 | 3.7 |
| Floricane yield (g/plant) | 2,292 | 2,680 |

TABLE 5

FOLIAGE CHARACTERISTICS

| Characteristic | 'NOBILITY' (3-Foliate) | 'GRANDEUR' (US PP20,459) (3-Foliate) |
|---|---|---|
| General: | | |
| Color of upper surface | RHS 137A Green group | RHS N137A Green group |
| Color of lower surface | RHS 190B Greyed-green group | RHS 190B Greyed-green group |
| Venation | Pinnate | Pinnate |
| Shape in cross section | Flat to slightly convex | Flat to slightly convex |
| Arrangement | Compound | Compound |
| Relief between veins (rugosity) | Medium | Strong |
| Glossiness | Weak | Weak |
| Number of leaflets per leaf | Mostly 3 | Always 3 |
| Total leaf length (cm) | 23.1 | 22.5 |
| Total leaf width (cm) | 24.0 | 23.4 |
| Terminal Leaflet: | | |
| Length (mm) | 139.7 | 127.5 |
| Width (mm) | 105.2 | 91.6 |
| Length/width ratio | 1.3 Longer than broad | 1.4 Longer than broad |
| Size | Medium to large | Medium to large |
| Shape | Cordate | Cordate |
| Shape of base | Cordate | Cordate |
| Shape of tip | Acuminate | Acuminate |
| Margins | Biserrate | Biserrate |
| Lateral Leaflet: | | |
| Length (mm) | 107.9 | 105.5 |
| Width (mm) | 67.9 | 65.1 |
| Length/Width Ratio | 1.6 Longer than broad | 1.6 Longer than broad |
| Rachis length (mm) | 35.8 | 36.2 |
| Rachis diameter (mm) | 2.45 | 1.92 |
| Rachis anthocyanin coloration of upper surface | RHS 184C | RHS 184A |
| Rachis anthocyanin intensity | Weak | Medium |

TABLE 5-continued

| FOLIAGE CHARACTERISTICS | | |
|---|---|---|
| Characteristic | 'NOBILITY' (3-Foliate) | 'GRANDEUR' (US PP20,459) (3-Foliate) |
| Orientation | Opposite | Opposite |
| Arrangement | Compound | Compound |
| Shape | Ovate | Ovate |
| Overlapping | Touching | Touching |
| Shape of the base | Rounded | Oblique rounded |
| Shape of the tip | Acuminate | Acuminate |
| Margins | Biserrate | Biserrate |
| Petiole: | | |
| Length (mm) | 45.90 | 59.00 |
| Width (mm) | 3.58 | 3.99 |
| Thorn presence | Yes | Yes |
| Thorn orientation | Erect | Erect |
| Anthocyanin coloration of upper surface | RHS 184C Greyed-purple group | RHS 184C Greyed-purple group |
| Anthocyanin intensity of upper surface | Absent to very weak | Weak |
| Stipule length (mm) | 9.31 | 10.23 |
| Stipule orientation | Erect | Erect to horizontal |

TABLE 6

| FLOWER CHARACTERISTICS | | |
|---|---|---|
| Characteristic | 'NOBILITY' | 'GRANDEUR' (US PP20,459) |
| Petal color (upper surface) | RHS 155C White group | RHS 155C White group |
| Petal color (lower surface) | RHS 155C White group | RHS 155C White group |
| Flower diameter (mm) | 24.92 | 22.55 |
| Petal Length (mm) | 7.07 | 6.42 |
| Petal width (mm) | 3.37 | 3.11 |
| Petal length/width ratio | 2.10 Much longer than broad | 2.06 Much longer than broad |
| Petal shape in cross section | Flat | Flat |
| Petal shape (overall) | Ovate | Ovate |
| Petal shape (apex) | Rounded | Rounded |
| Petal shape (base) | Attenuate | Attenuate |
| Petal margin | Entire | Entire |
| Petal texture | Glabrous | Glabrous |
| Number of petals per flower | 5.5 | 5.2 |
| Number of sepals per flower | 5.5 | 5.2 |
| Sepal length (mm) | 10.01 | 11.20 |
| Sepal width at base (mm) | 5.22 | 6.49 |
| Sepal shape | Widely deltate | Widely deltate |
| Sepal shape (apex) | Acuminate | Acuminate |
| Sepal coloration (upper surface) | RHS 144A | RHS 144B |
| Sepal coloration (lower surface) | RHS 144B | RHS 144C |
| Sepal margin | Entire | Entire |
| Sepal texture | Slightly pubescent | Slightly pubescent |

TABLE 6-continued

| FLOWER CHARACTERISTICS | | |
|---|---|---|
| Characteristic | 'NOBILITY' | 'GRANDEUR' (US PP20,459) |
| Number of stamens per flower | 81 | 105 |
| Filament length (mm) | 4.62 | 4.45 |
| Filament color | RHS 155C White group | RHS 155C White group |
| Pollen quantity | Medium | Medium |
| Pollen color | RHS 196D | RHS 196D |
| Anther length (mm) | 1.10 | 0.79 |
| Anther diameter (mm) | 0.50 | 0.49 |
| Anther coloration (pre-dehiscence) | RHS 155C | RHS 155C |
| Anther coloration (post-dehiscence) | RHS 165B | RHS 165B |
| Stigma shape | Lobed | Lobed |
| Stigma length (mm) | 0.11 | 0.10 |
| Stigma diameter (mm) | 0.42 | 0.40 |
| Stigma coloration | RHS 145D | RHS 145D |
| Style length (mm) | 2.55 | 2.03 |
| Style diameter (mm) | 0.41 | 0.39 |
| Style coloration | RHS 145D | RHS 145D |
| Ovule length (mm) | 1.55 | 1.51 |
| Ovule diameter (mm) | 1.46 | 1.40 |
| Ovule coloration | RHS 145B | RHS 145B |
| Pedicle length (mm) | 21.56 | 23.86 |
| Pedicle diameter (mm) | 1.33 | 1.47 |
| Pedicle anthocyanin coloration | RHS 182B | RHS 178A |
| Pedicle anthocyanin intensity | Absent to very weak | Medium |
| Relative number of pedicel thorns | 23.5 Many | 16.2 Medium |
| Peduncle anthocyanin presence | Present | Present |
| Peduncle anthocyanin coloration | RHS 182C Greyed-purple group | RHS 184A Greyed-purple group |
| Peduncle anthocyanin intensity | Absent to very weak | Medium |

TABLE 7

| PEST AND DISEASE REACTIONS | | |
|---|---|---|
| Characteristic | 'NOBILITY' | 'GRANDEUR' (US PP20,459) |
| Spotted wing drosophila (*Drosophila suzukii*) | Susceptible | Susceptible |
| Two-spotted spider mite (*Tetranychus urticae*) | Susceptible | Susceptible |
| Grey fruit mold (*Botrytis cinerea*) | Susceptible | Susceptible |
| Powdery mildew (*Podosphaera aphanis var. aphanis*) | Moderately susceptible | Moderately susceptible |
| Yellow rust (*Phragmidium rubi-idaei*) | Moderately susceptible | Moderately susceptible |

I claim:

1. A new and distinct variety of raspberry plant named 'NOBILITY', as herein described and illustrated by the characteristics set forth above.

* * * * *